United States Patent [19]

Laas et al.

[11] Patent Number: 4,740,283

[45] Date of Patent: Apr. 26, 1988

[54] PULSED-FIELD GRADIENT GEL ELECTROPHORETIC APPARATUS

[75] Inventors: William A. Laas, San Francisco, Calif.; David Patterson; Katheleen J. Gardiner, both of Denver, Colo.

[73] Assignee: University Patents, Inc., Westport, Conn.

[21] Appl. No.: 5,278

[22] Filed: Feb. 3, 1987

Related U.S. Application Data

[63] Continuation-in-part of Ser. No. 833,691, Feb. 27, 1986, abandoned.

[51] Int. Cl.$^4$ .................... G01N 27/26; G01N 27/28
[52] U.S. Cl. ............................ 204/182.8; 204/299 R; 204/183.1
[58] Field of Search ............ 204/299 R, 300 R, 182.1, 204/182.8, 182.9, 183.1, 180.1

[56] References Cited

U.S. PATENT DOCUMENTS

| | | | |
|---|---|---|---|
| 3,506,554 | 4/1970 | Broome | 204/299 R |
| 4,148,703 | 4/1979 | Trop et al. | 204/299 R X |
| 4,473,452 | 9/1984 | Cantor et al. | 204/182.8 |
| 4,541,910 | 9/1985 | Davis, III et al. | 204/299 R X |
| 4,569,741 | 2/1986 | Pohl | 204/299 R X |

OTHER PUBLICATIONS

M. W. Hunkapiller et al., "Isolation of Microgram Quantities of Proteins from Polyacrylamide Gels for Amino Acid Sequence Analysis", Methods in Enzymology, vol. 91 (1983) Academic Press Inc., pp. 228–236.

Patent Abstracts of Japan, vol. 10, No. 198 (P-476) [2254], Jul. 11, 1986.

Primary Examiner—John F. Niebling
Assistant Examiner—Starsiak, Jr. John S.
Attorney, Agent, or Firm—George M. Yahwak; David N. Koffsky

[57] ABSTRACT

A pulsed-field gradient gel electrophoretic apparatus is described wherein a free standing gel is employed. Electrode arrays are oriented to provide three dimensional fields across the face of the gel rather than in the plane of the gel. The electrodes produce three dimensional fields which are orthogonally oriented with respect to each other and cause the molecules to proceed down the lanes in the gel in a generally saw-tooth manner oscillating between the surfaces thereof. Alternately, three dimensional, electric fields are arranged at angles greater than 90° to one another across the face of the gel in separating the molecules, following which transfer electrodes are substituted for the separation electrodes in order to transfer the molecules from their separation lanes onto a separate substrate.

17 Claims, 5 Drawing Sheets

PULSED-FIELD GRADIENT GEL ELECTROPHORETIC APPARATUS

REFERENCE TO RELATED APPLICATION

This application is a continuation-in-part of earlier filed Ser. No. 833,691, filed Feb. 27, 1986, now abandonded.

This invention relates to electrophoresis; and more particularly relates to pulsed-field electrophoretic systems.

BACKGROUND AND FIELD OF THE INVENTION

Electrophoresis is a technique by which particles such as mixtures of macromolecules are moved through a gel matrix by an electric field. It is a widely used technique for quantitative analysis and for separation, recovery and purification of certain macromolecular species. It is widely used for the study of proteins, nucleic acids and chromosomes. Until recently, it has been difficult to electrophoretically separate very large particles.

Recently, pulsed-field gradient, gel electrophoretic systems have come into being which make possible the resolution of large DNA molecules. These systems, in essence, repetitively alter the field direction applied to a gel containing the DNA molecules. This alteration of the field direction produces the separation of the molecules because the molecules, depending upon their molecular weight (or contour length), vary in the amount of time required to change direction. Several different designs for employing pulsed-field techniques have been recently reported. In U.S. Pat. No. 4,473,452 to C. R. Cantor et al, a planar gel is employed which is oriented horizontally on the bottom of a buffer chamber. Several power supplies allow different voltages to be applied parallel to the plane of the gel to produce alternating fields. The design employs electrode arrays constructed from a series of vertical lengths of platinum wire in which each is isolated from the others by a diode array. Another design, described by Carle, G. F. et al, "Nucleic Acid Research", (1984), Vol. 12, No. 14, pp. 5647–5664, uses a similar structure but rather employs a continuous length of platinum wire for each electrode and avoids the use of a diode array. Though this design allows substantial short circuiting, it does perform well. Neither design, however, is able to produce gel lanes that are exposed to equivalent electrical fields and, thus, the nucleic acid samples move in a complex trajectory through the gel making subsequent interpretation somewhat difficult.

Accordingly, it is an object of this invention to provide a pulsed-field gradient, gel electrophoretic apparatus wherein all separation lanes are exposed to equivalent field strengths and orientations.

It is a further object of this invention to provide a pulsed-field gradient gel electrophoretic apparatus which provides separation lanes which are easily readable and wherein the molecules being separated follow a linear and well defined path.

It is a further object of the present invention to provide for a novel and improved electrophoretic apparatus which achieves increased resolution of the molecules within each separation lane; and further wherein the apparatus is so constructed and arranged as to be interchangeable for use in the separation and transfer of molecules from their separation lanes.

SUMMARY OF THE INVENTION

In accordance wtih the above objects, a pulsed-field gradient gel electrophoretic apparatus is provided wherein a free standing gel is employed. Electrode arrays are oriented to provide three dimensional fields across the face of the gel rather than in the plane of the gel. The electrodes produce three dimensional fields which are orthogonally oriented with respect to each other and cause the molecules to proceed down the lanes in the gel in a generally saw-tooth manner oscillating between the surfaces thereof.

In an alternate form of invention, three dimensional fields are arranged at angles greater than 90° to one another, the maximum fields intersecting the upper end of a free standing gel to achieve excellent resolution of the molecules. In order to provide for efficient collection of the molecules following separation, transfer electrodes are substituted for the gel run electrodes in the same housing and, using the same source of power as for the gel run electrodes, are capable of transferring the molecules from the gel onto a separate substrate.

DETAILED DESCRIPTION OF THE PREFERRED EMBODIMENT

Figure 1:
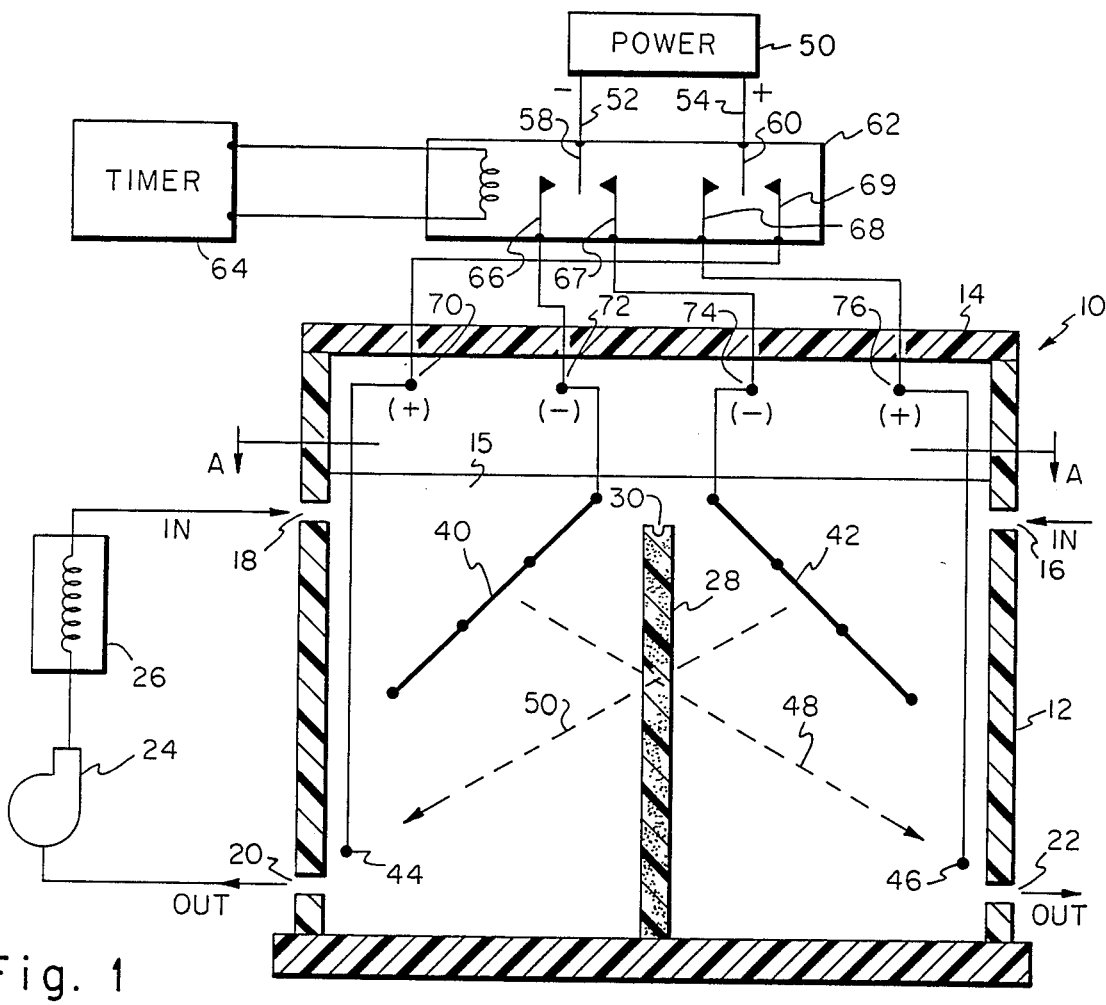
FIG. 1 is a cross-sectional view of the invention.
Figure 2:
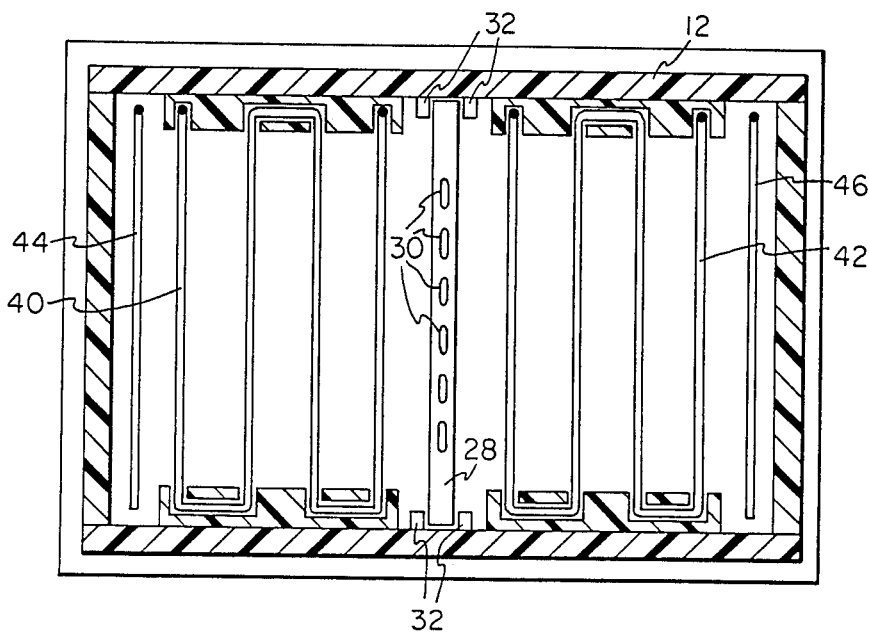
FIG. 2 is a sectional view taken along line AA.

Referring now to FIGS. 1 and 2, electrophoretic apparatus 10 is housed within gel box 12, the top portion 14 of which is readily removable. Apparatus 10 is filled with buffer 14 and is provided with several buffer inlets 16 and 18 and several buffer outlets 20 and 22. Both buffer outlets 20 and 22 feed to a pump 24 and into a refrigerated waterbath and heat exchanger 26. From there, cooled buffer 15 is recirculated back into gel box 12.

Electrophoretic gel 28 is self-supporting and is provided with a plurality of wells 30 as is conventional. Gel 28 is produced by casting it between glass plates, and, after cooling, the plates are removed and the gel is positioned vertically in gel box 12. It is supported within slots formed between two posts 32 on the inner surfaces of box 12 (see FIG. 2). A 1% agarose gel ($\frac{1}{4}$" thick) is sturdy enough to stand upright in the slots without supporting plates.

Electric fields are generated in alternating directions and at acute angles through the faces of gel 28 by two equivalent arrays of platinum wire electrodes 40, 46, and 42, 44. Electrodes 40 and 42 are each formed from a single length of platinum wire strung back and forth in a shoe lace fashion to create four exposed horizontal stretches of wire. The intervening segments of wire are covered by short pieces of tubing which act as insulating shields. As viewed in FIG. 1, the planes of electrodes 40 and 42 are approximately at right angles with respect to each other and are oriented orthogonally to electrodes 46 and 44 respectively. It can thus be seen by one skilled in the art that the application of opposite voltages between electrodes 40 and 46, for example, will create a three dimensional field across and through the surface of gel 28 which field will be oriented generally in the direction indicated by arrow 48. A similar field 50 will be created by the proper energization of electrodes 42 and 44. It can be seen from this design that all of the gel lanes in gel 28 are exposed to equivalent electrical fields and that samples placed within wells 30 move straight down the lanes directly below each loading well.

Power supply 50 has both negative and positive output lines 52 and 54 which are connected to armatures 58 and 60 of double pole, double throw relay 62. The position of armatures 58 and 60 is controlled by switching timer 64 which is connected to the coil within relay 62. When the output from timer 64 is energized, relay armatures 58 and 60 connect to contacts 66 and 68 which in turn apply negative and positive potentials via terminals 72 and 76 to electrodes 40 and 46 respectively. When the output from timer 64 is deenergized, armatures 58 and 60 connect to contacts 67 and 69 causing negative and positive potentials to be applied via contacts 75 and 70 respectively to electrodes 42 and 44.

With gel 30 precisely centered in box 12, and the electrode pairs delivering equivalent pulses of electrical charge for equal amounts of time, the net effect is for the samples being separated to move from the top to the bottom of gel 28. Additionally, and importantly, the alternation of the field direction brings about the separation of large DNA molecules which would otherwise comigrate as a broad band as in conventional single field electroporesis.

The above mentioned apparatus has been constructed and operated successfully. The system employed: an ISCO Model 493 Power Supply; a double-pole, double-throw relay activated by a Gray Lab Model 625 Timer; a buffer recirculation and cooling system consisting of an oscillating pump (Cold-Parmer), a refrigerated water bath (Lauda Model RM 6), and a heat exchanger made of two twelve foot loops of polyethylene tubing ($\frac{1}{4}$") that were coiled side by side and submerged in a water filled styrofoam box. One loop circulated coolant between the water bath and the box, and the other loop circulated buffer between the heat exchanger box and the gel chamber. The gel box was constructed from $\frac{1}{4}$" clear plexiglass sheet and had internal dimensions of 6"×3"×6.5". The agarose gel dimensions were 7.6 cm wide by 10 cm tall by 0.64 cm thick. A 1% gel was employed. The platinum wire was 28 gauge.

As above stated, a novel and most important feature of this invention is that the electric field is caused to pass through the thickness of the gel rather than through its planar dimension as in prior art designs, thereby allowing each lane to be exposed to identical field strengths with the movement of separated components being strictly contained within the gel lanes. The frequency of alteration of field direction determines the size, class of molecules to be resolved. For most applications involving fragments from 200 to 2000 kilobases, pulse times of 40 to 60 seconds were used.

A number of alterations may be made to the basic design of the invention. If it is desired to alter the field strength profiles along the separation lanes, both electrode 40 and 42 may be altered to fit concave or convex curvatures so that as sample components traverse down the length of the gel, they will enter regions of gradually decreasing field strengths. Furthermore, while electrode arrays 40 and 42 are shown in a fixed orientation, they may be made movable to allow the choice of a spectrum of angles of intersection of the electric fields. Additionally, while gel 28 is shown free standing, it may be alternatively cast within a frame, movable in the gel box so that the gel can be repositioned with respect to the electrodes at various intervals during the separation procedure. In this regard, it is also contemplated that electrodes 40 and 42 may be altered so as to focus the electrical field on a smaller select region of the gel (e.g. near the sample loading wells) rather than its entire length. In such an arrangement, the gel would be moved vertically through the intersecting fields by a variable speed mechanical drive mechanism such that the gel would be exposed to the fields, a portion at a time, as it is moved. This structure allows the separation to be optimized by enabling selection of a range of voltages, pulse times, drive speeds, etc. Of course, it is also contemplated in such an arrangement that electrodes 40 and 42 (and 44 and 46) could be made movable while gel 28 is fixed.

DETAILED DESCRIPTION OF ALTERNATE FORM OF THE PRESENT INVENTION

Figure 5:
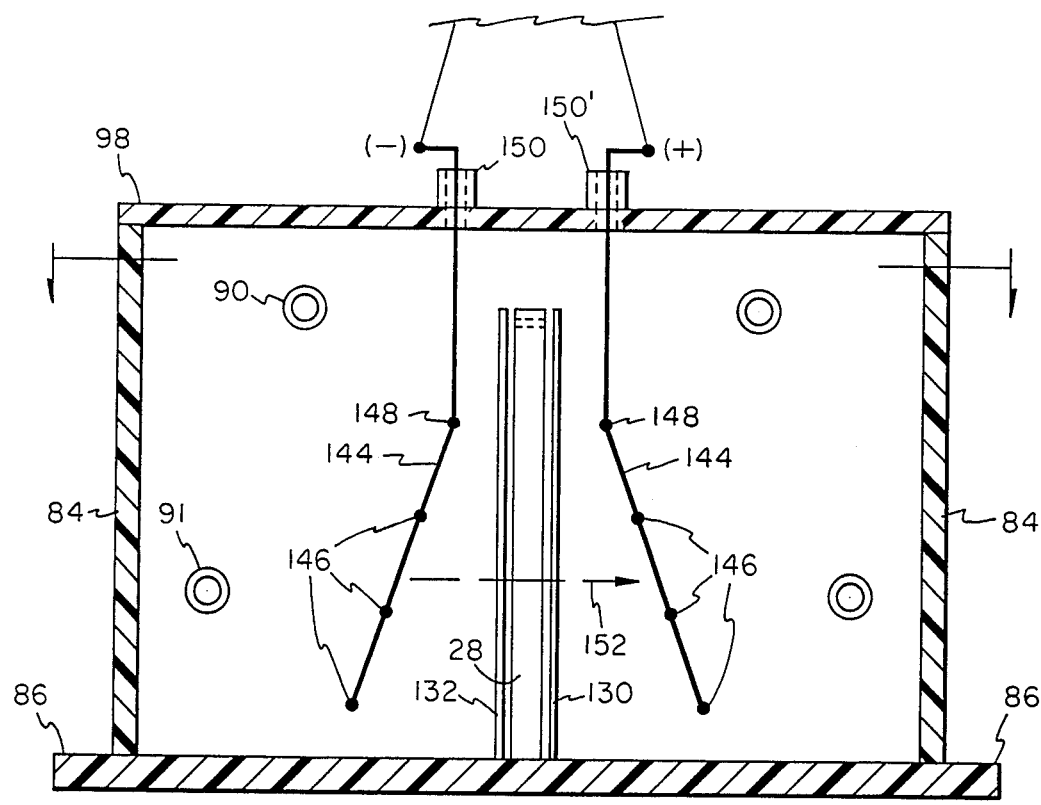
FIG. 5 is a cross-sectional view of an alternate form of invention showing an array of transfer electrodes.
Figure 6:
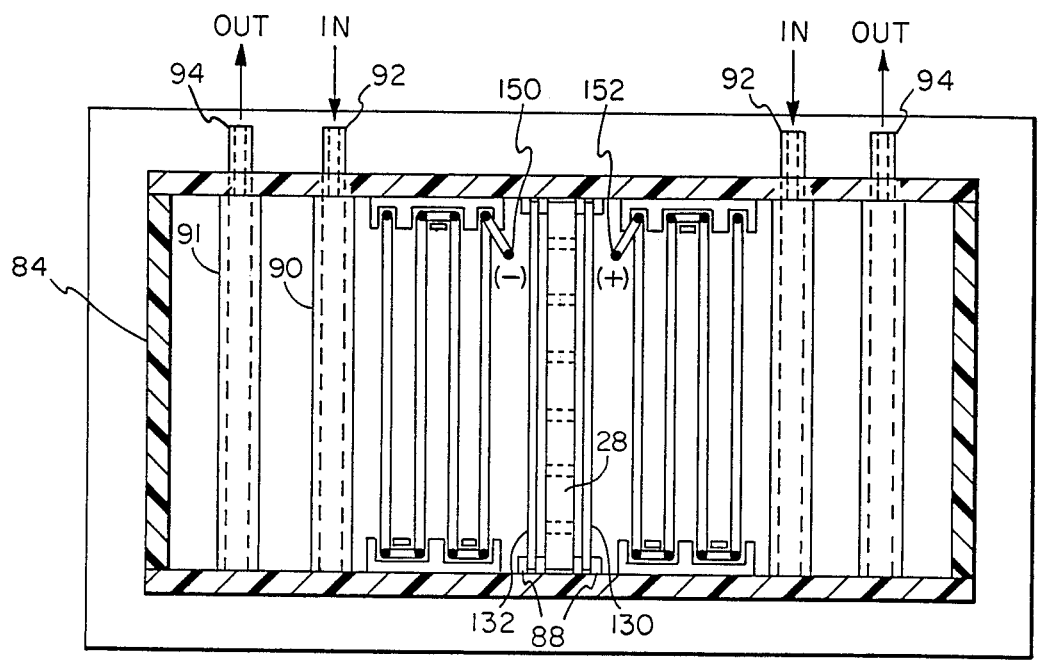
FIG. 6 is a top plan view of the alternate form as shown in FIG. 5.
Figure 7:
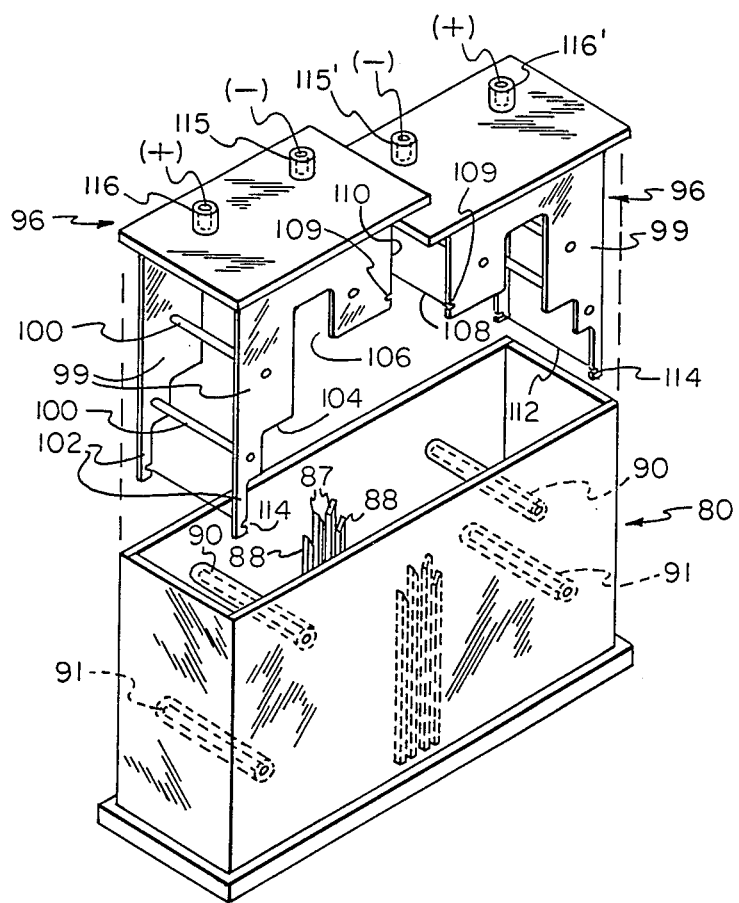
FIG. 7 is an isometric view in exploded form illustrating the insert assemblies for the gel run electrodes.
Figure 8:
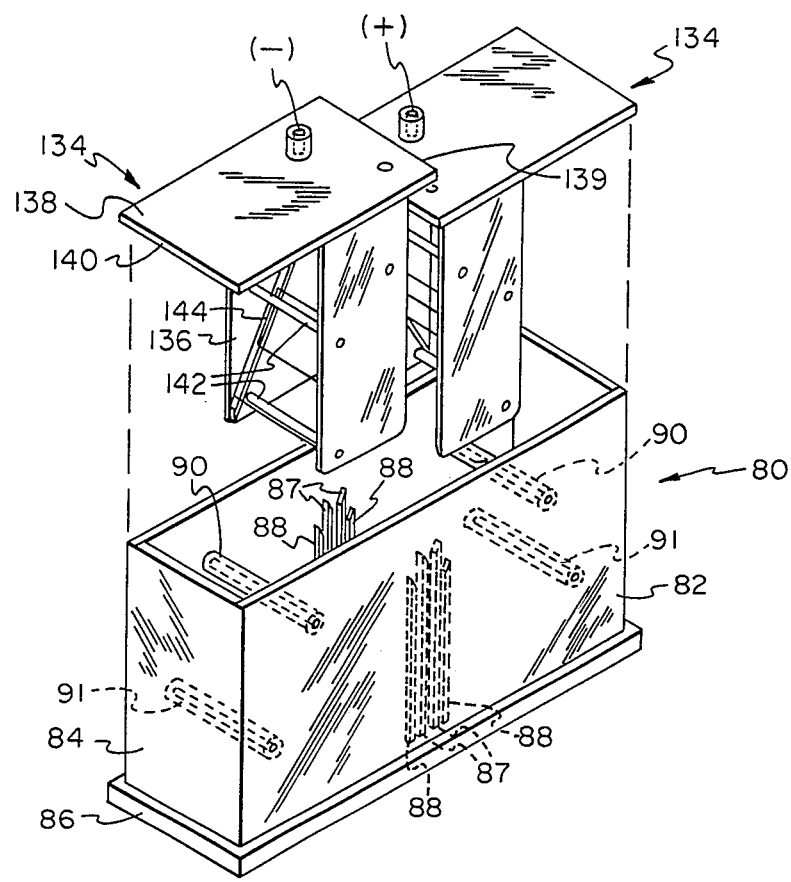
FIG. 8 is an isometric view in exploded form illustrating the insert assemblies for the transfer electrodes.

An alternate form of invention is illustrated in FIGS. 3 to 8 wherein a gel box 80 is of elongated rectangular configuration having opposite sidewalls 82, opposite end walls 84 and a base 86. First pairs of inner posts 87 intrude from opposite sidewalls 82 in aligned relation to one another, the inner posts 87 on each sidewall disposed in closely spaced, facing relation to one another for insertion of a self-supporting gel medium 28 within the slots formed between the inner posts 87 in the same manner as described with reference to FIGS. 1 and 2. As illustrated in FIGS. 7 and 8, second pairs of outer posts 88 protrude inwardly from opposite sidewalls in aligned relation to one another, the outer posts 88 being somewhat shorter than the inner posts 87 and, in a matter to be hereinafter described, spaced apart a distance to best accommodate placement of the gel 28 during the transfer process.

Figure 3:
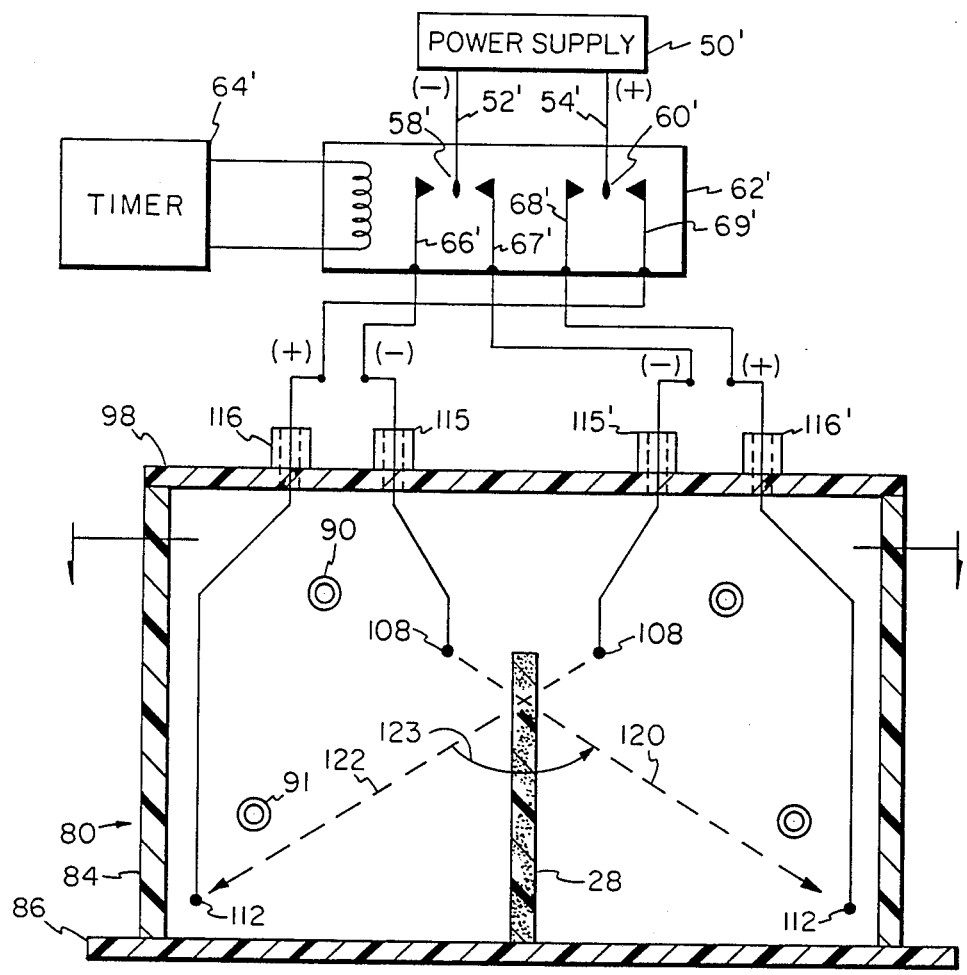
FIG. 3 is cross-sectional view of an alternate form of the invention.
Figure 4:
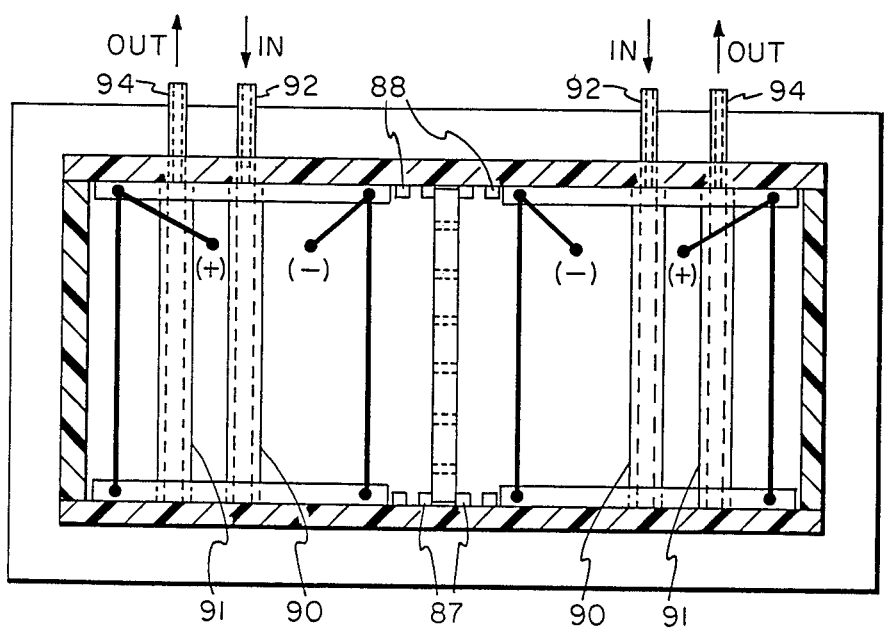
FIG. 4 is a top plan view of the form of invention shown in FIG. 3.

The gel housing or box 80 as described is open at its upper end, and buffer circulation ports in the form of upper and lower perforated tubes 90 and 91 extend between opposite sidewalls 82 and are arranged symmetrically on either side of the posts 87 and 88. As shown in FIGS. 3 and 4, buffer inlets 92 communicate with the upper ports 90 and lower buffer outlets 94 communicate with the lower ports 91. In the manner described with reference to FIGS. 1 and 2, a refrigerated water bath and heat exchanger are arranged in a closed circulation system with the buffer inlets 92 and outlets 94 for recirculation of a buffer solution through the housing in order to maintain a constant temperature of the buffer solution within the housing 80. In order to subject the gel 28 to alternating pulsed fields, a pair of gel run insert assemblies 96 are constructed for removable insertion into the common housing 80, as illustrated in FIG. 7. Each insert assembly is of corresponding construction and includes a top 98, a pair of downwardly directed, spaced sidewalls 99 which extend from the undersurface of the top 98, and a pair of transverse support members 100 which extend between the sidewalls 99 in assembled relation to the housing 80. The sidewalls 99 are spaced apart for a distance to clear the sidewalls 82 when inserted into the housing 80. Each sidewall 99 includes a downwardly extending leg 102 arranged for extension along the end wall 84 of the housing, a stepped portion 104 terminating above the lower circulating port 91 and a recessed area 106 of inverted U-shaped configuration to receive the upper circulating port 90. Each of the insert assemblies 96 includes an upper electrode wire 108 extending between notched portions 109 in front edge 110 of the sidewalls 99; and a lower electrode wire 112 extends between notched portions 114 in lower leg portions 102 in the sidewalls 99 of each insert assembly. The tops 98 of the insert assemblies are dimensioned to overlie the upper edge of the housing and, when inserted into the housing, to fit snugly into abutting relation to one another such that the leg portions 102 bear against opposite end walls 84 of the housing. Each upper electrode wire 108 is electrically connected, as illustrated in FIG. 3, to a negative terminal 115 or 115' on the top 98 of each insert assembly. In turn, the lower electrode wire 112 is electrically connected to a positive terminal 116 or 116' on the top 98 of each insert assembly.

As best seen from a consideration of FIG. 3, the negative or upper electrodes 108 are spaced equidistant from the center line of the gel 28 and at a height or location which is preferably spaced slightly above the well or top surface of the gel 28. The lower, positive electrodes 112 are spaced equidistant from the center line of the gel 28 and in a horizontal plane spaced above the lower edge of the gel or base 86 of the housing. Preferably each electrode 108 and 112 is composed of a single length of platinum wire with opposite ends of the wire inserted within the notches 109 or 114 as described, and the wire is shielded where necessary at the connecting ends and from one of the notched ends to the respective terminals 115, 115', and 116, 116'. As in the form of FIGS. 1 and 2, the wires extend in a horizontal direction in spaced parallel relation to the vertical, free standing gel 28. In response to the application of voltages alternately between each negative electrode 108 on one side of the gel 28 and each positive electrode 112 on the opposite side of the gel, electric fields are created in which the maximum strength or intensity of the fields, as represented at 120 and 122, intersect the upper end of the gel and will pass downwardly at an acute angle through the thickness of the gel. However, the angular relationship established between electrical fields as represented by 120 and 122 is greater than an orthogonal relationship.

The increased angle between the fields has been found to achieve higher resolution than heretofore possible and is capable of separating larger molecules when subjected to voltages in the range of 200 to 250 volts. Notwithstanding the increased voltage, less current is required; yet will separate larger molecules in the gel. For example, the included angle 123 between the maximum fields at 120 and 122 is on the order of 110° to 120°, as illustrated in FIG. 3. In this relation, it is to be understood that the overall fields established pass through the entire length and breadth of the gel but are of reduced intensity in proceeding downwardly and away from the maximum fields 120 and 122.

In the same manner as shown in the form of FIGS. 1 and 2, the power supply 50' has negative and positive lines 52' and 54' which are connected to armatures 58' and 60', respectively, of a double pole, double throw relay 62'. Switching timer represented at 64' is connected to a coil within the relay 62' and, when the output from the timer 64' is energized, the relay armatures 58' and 60' are closed through contacts 66' and 68' so as to apply negative and positive potentials via the terminals 115 and 116 to the wires 108 and 112, respectively, to establish the electrical field 120. When the output from the timer 64' is deenergized, the armatures 58' and 60' are switched to contacts 67' and 69' to cause the voltage to be applied via terminals 115' and 116' to establish the electrical field 122. Again, when the gel 28 is centered between the negative wires 108 and 112, alternating pulses are applied to each set of electrodes for equal amounts of time and in the direction of the fields represented by 120 and 122 to cause the DNA molecules to advance in a somewhat serpentine path along the lanes established from the top to the bottom of the gel 28.

Following electrophoresis as described, the insert assemblies 96 are removed, and the gel 28 is removed from the gel box 80 for treatment in accordance with conventional procedures as a preliminary to transfer or electroblotting of the DNA molecules onto a membrane or filter. Typically, in this procedure, the gel is stained with ethidium bromide so that the DNA can be flouresced under ultraviolet light. It is then soaked in a sodium hydroxide solution to denature the DNA molecules and open up the double stranded DNAs. It is then neutralized to reduce the Ph and equilibrated to remove any salt or sodium hydroxide present. The gel is then sandwiched between two surfaces, one being a membrane such as "Zeta-Probe" manufactured and sold by Bio-Rad Laboratories, of Richmond, Calif., the membrane being designated at 130. Backing members 132 are applied to opposite planar surface of the gel and membrane, and the gel assembly is then repositioned in the housing 80 between the outer posts 88.

As shown in FIG. 8, transfer insert assemblies 134 are placed in the gel housing 80 on opposite sides of the posts 88. Each insert assembly 134 correspondingly includes opposite sidewalls 136 of generally rectangular configuration extending downwardly from the underside of a generally rectangular top 138, the sidewalls 136 being spaced inwardly of the edges of the top 138 a sufficient distance that they will just clear the inner surfaces of the sidewalls 82 when inserted into the gel housing 80. In addition, the sidewalls 136 are positioned relatively near an inner facing end 139 of the top and relatively away from the opposite end 140. Reinforcing bars 142 extend at spaced intervals between the sidewalls 136, two of the bars 142 being disposed at upper and lower ends of inclined electrode support ribs or holders 144 which protrude inwardly from opposed, inner facing surfaces of the sidewalls 136 and in aligned relation to one another. As shown in FIG. 5, an electrode array as designated at 146 comprises a single length of wire which is advanced back and forth in horizontal courses between the upper and lower ends of the holders 144. The holders 144 are notched or grooved to receive diagonally extending segments of the wire so as to act as insulating shields along opposite ends of the stretches of wire. In order to assure consistent positioning of the insert assemblies, the tops 138 are dimensioned such that their edges will just overlap the upper edge of the housing 80 when the sidewalls 136 are inserted into the housing with the rearward edges of the sidewalls 136 away from the posts 88 in front of the upper buffer circulating ports 90.

As shown in FIGS. 5 and 6, an upper terminal end of each wire, designated at 148, is connected into a terminal 150 or 150', the terminal 150 being connected to the negative side of the power supply 50' and terminal 150' being connected to the positive side of the power supply 50'. In the relationship illustrated, the lattice structure or electrode array in each insert assembly inclines downwardly and away from the uppermost stretch of wire. The electrode array of each insert assembly when positioned in the gel housing 80 is spaced equidistant from the center line of the gel and creates a three-dimensional field which extends in the horizontal direction from the negative to the positive arrays, as represented in dotted form at 152. The gradual divergence of the electrode arrays 146 away from the upper end of the gel is important in order to dislodge or transfer the larger DNA molecules at the upper end of the gel and, in diverging downwardly and away from the gel, establish a gradual decrease in voltage across the thickness of the gel from the upper to the lower end of the gel 28.

In the transfer procedure as shown, in accordance with conventional practice, the electrical field is applied in one direction only through the thickness of the gel in order to transfer the DNA molecules from the gel onto the substrate as defined by membrane 130. Accordingly, it is important that the membrane 130 be positioned on one planar surface of the gel away from the negative electrode.

As in the gel run procedure, the buffer is continuously recirculated through the housing to maintain a constant temperature. The same power supply 50' as employed for electrophoresis may be used in the transfer apparatus to apply a voltage in the direction indicated across the gel assembly. Typically the voltage level applied across the gel assembly is on the order of 120 volts and is applied for approximately 2 hours to assure complete transfer of the DNA molecules. The interchangeable insert assemblies 96 and 134 for electrophoresis and transfer, respectively, permit utilization of the same gel housing 80 while achieving optimum angles between the electrodes for each procedure. Nevertheless, it will be evident that the electrode and wires may be mounted in separate housings by direct attachment to the holders 144 on the sidewalls 82 of the housing 80 itself while establishing the desired angular relationship between the electrodes, for example, in a manner similar to that described with respect to FIGS. 1 and 2. In this relation, the single electrode wire 108 for the negative electrode affords greater latitude in the choice of the angular relationship between the electric fields than the electrode array as shown in FIGS. 1 and 2. Thus, the angular relationship between the maximum fields 120 and 122 may be varied by shifting either the negative electrode 108 or positive electrode 112 as long as the gel is centered between the electrodes and the entire fields traverse the full length of the gel. Accordingly, when the field angle 123 is increased, the length of the gel box 80 must be increased to maintain the positive electrodes 112 close enough to the lower end of the gel to assure that the fields will traverse the entire length of the gel; and it is equally important that the maximum fields 120 and 122 intersect the upper ends of the lanes or bands containing the DNA molecules to encourage downward movement and optimum resolution of the molecules along each lane or band. Generally, it has been found that increasing the maximum field angle 123 beyond 90° and into the range of 110° to 120° makes possible the movement or separation of larger molecules on the order of 2,000,000 base pairs. The resolution or movement of molecules larger than 2,000,000 base pairs may be achieved by increasing the maximum field angle 123 beyond 120° when combined with the appropriate adjustment or selection of voltage and pulse time.

It is therefore to be understood that the above and other modifications and changes may be made in the alternate forms of invention as herein set forth and described without departing from the spirit and scope of the present invention as defined in the appended claims.

We claim:

1. Electrophoretic separation apparatus comprising:
    a medium for supporting particles to be separated, said medium exhibiting at least a pair of opposed generally planar faces separated by a thickness of medium small in relation to the dimension of said faces and including one or more separation track(s);
    first electrode means positioned about said medium for applying, upon energization, a first electric field across said separation track(s), the direction of said first field intersecting both said planar faces and oriented at an angle which is acute with respect to a first said planar face;
    second electrode means positioned about said medium for applying, upon energization, a second electric field across said separation track(s), the direction of said second field intersecting both said planar faces and oriented at an angle which is acute with respect to a second said planar face; and
    means for alternately and repetitively energizing said first and second electrode means.

2. The invention as defined in claim 1 wherein said first and second field directions are approximately orthogonal with respect to each other.

3. The invention as defined in claim 2, wherein each said first and second electrode means comprises two portions, one portion juxtaposed to one of said pair of opposed generally planar faces of said medium and the other portion to a second of said pair of opposed generally planar faces of said medium.

4. The invention as defined in claim 3 wherein said one portion includes a conductor grid which produces a three dimensional field configuration which substantially encompasses the length of all separation tracks.

5. The invention as defined in claim 1 wherein said medium is a gel-like, planar substance through which said particles may move and has sufficient physical rigidity to be free standing.

6. The invention as defined in claim 5 wherein each said electrode means comprises a multi-conductor, substantially planar array, juxtaposed next to one of said pair of opposed generally planar faces of said medium with a corresponding oppositely poled electrode positioned opposite a second of said pair of opposed generally planar faces of said medium.

7. Electrophoretic apparatus comprising:
    a medium for supporting particles to be separated, said medium exhibiting at least a pair of opposed generally planar faces separated by a thickness of medium small in relation to the dimension of said faces and including one or more separation track(s) for advancement of the particles from one end to an opposite end of said separation track(s);
    first electrode means positioned about said medium for applying, upon energization, a first electric field across said separation track(s), the direction of said first field intersecting both said planar faces adjacent to the one end of said separation track(s) and oriented at an angle which is acute with respect to a first said planar face;

second electrode means positioned about said medium for applying, upon energization, a second electric field across said separation track(s), the direction of said second field intersecting both said planar faces adjacent to the one end of said separation track(s) and oriented at an angle which is acute with respect to a second said planar face, the included angle between said electric fields being at least 90°; and means for alternately and repetitively energizing said first and second electrode means.

8. The invention as defined in claim 7 wherein said first and second electrode means have maximum fields at an included angle in the range of 90° to 120° to one another.

9. The invention as defined in claim 8, wherein said first and second electrode means each comprises a negative electrode disposed adjacent to one planar face of said medium and a positive electrode disposed opposite to the other planar face of said medium, the distance between each said positive electrode and said medium being greater than the distance between each said negative electrode and said medium.

10. The invention as defined in claim 7 wherein said medium is an upright, gel-like, planar substance centered between said first and second electrode means, said medium having wells in communication with the one end of said separation track(s), said first and second electric fields extending in a downward angular direction through the thickness of said medium between the opposite ends of said separation track(s).

11. The invention as defined in claim 10, said first and second electrode means each defined by at least one wire extending horizontally in spaced parallel relation to said medium.

12. The invention as defined in claim 10, said apparatus including a common housing having medium support means for removably supporting said planar medium symmetrically between said negative and positive electrodes, electrode support means for removably supporting said negative and positive electrodes in said housing, and transfer electrode means including means removably positioning said transfer electrode means in said housing for applying upon energization a uni-directional field across said medium.

13. The invention as defined in claim 12, said transfer electrode means operative to apply a progressively reduced voltage drop across said medium from one end to the opposite end of said medium.

14. The invention as defined in claim 13, said transfer electrode means including positive and negative electrodes each in the form of a multi-conductor array diverging downwardly and away from opposite planar faces of said medium.

15. The method of performing separation and transfer of macromolecular particles from separation track(s) of a supporting medium onto a substrate comprising the steps of:

(1) orienting said medium in a vertical plane symmetrically between intersecting first and second electrical fields;

(2) alternately and repetitively directing said first and second electrical fields at downwardly directed angles through the upper end of said supporting medium until said macromolecular particles are separated along said separation track(s);

(3) applying a substrate to one planar surface of said medium; and (4) exposing said medium to a third electric field extending across said medium in a direction causing said macromolecular particles to be transferred from said separation track(s) onto said substrate.

16. The method according to claim 15, in which the included angle between said first and second electric fields is at least 90°.

17. The method according to claim 15, characterized in step (4) by applying a progressively reduced voltage drop across said medium from the upper end to the lower end thereof.

* * * * *

UNITED STATES PATENT AND TRADEMARK OFFICE
CERTIFICATE OF CORRECTION

PATENT NO. : 4,740,283

DATED : April 26th 1988

INVENTOR(S) : WA Laas, D Patterson and KJ Gardiner

It is certified that error appears in the above-identified patent and that said Letters Patent is hereby corrected as shown below:

Column 1, line 15, please insert the following paragraph:

-- This invention was made in part with government funding under National Institutes of Health contracts no. AG00029 and HD13423. Accordingly, the government has certain statutory rights in this invention. --

Signed and Sealed this

Sixteenth Day of February, 1993

*Attest:*

STEPHEN G. KUNIN

*Attesting Officer* — Acting Commissioner of Patents and Trademarks